United States Patent [19]
Kulagowski et al.

[11] Patent Number: 5,792,768
[45] Date of Patent: Aug. 11, 1998

[54] ANTIPSYCHOTIC BENZIMIDAZOLE DERIVATIVES

[75] Inventors: Janusz Jozef Kulagowski, Bishops Stortford; Paul David Leeson, Cambridge, both of Great Britain

[73] Assignee: Merck, Sharp & Dohme Limited, Hoddesdon, England

[21] Appl. No.: 525,696

[22] PCT Filed: Mar. 23, 1994

[86] PCT No.: PCT/GB94/00607

§ 371 Date: Dec. 20, 1995

§ 102(e) Date: Dec. 20, 1995

[87] PCT Pub. No.: WO94/22839

PCT Pub. Date: Oct. 13, 1994

[30] Foreign Application Priority Data

Mar. 30, 1993 [GB] United Kingdom ............... 9306578

[51] Int. Cl.$^6$ .................. A61K 31/495; C07D 403/06
[52] U.S. Cl. ................................. 514/255; 544/370
[58] Field of Search ............... 514/255; 544/370

[56] References Cited

U.S. PATENT DOCUMENTS 3,472,854  10/1969  Archer .................. 260/268
5,432,177  7/1995  Baker et al. ............ 514/253

FOREIGN PATENT DOCUMENTS 0 241 053     10/1987   European Pat. Off. .
0 441 631 A1   2/1991   European Pat. Off. .

Primary Examiner—Phyllis G. Spivack
Attorney, Agent, or Firm—Melvin Winokur

[57] ABSTRACT

A class of benzimidazole derivatives, substituted at the 2-position by a substituted piperazinylmethyl or piperazinylethyl moiety, are antagonists of dopamine receptor subtypes within the brain, having a selective affinity for the dopamine $D_4$ receptor subtype over other dopamine receptor subtypes, and are accordingly of benefit in the treatment and/or prevention of psychotic disorders such as schizophrenia whilst manifesting fewer side-effects than those associated with classical neuroleptic drugs.

9 Claims, No Drawings

ANTIPSYCHOTIC BENZIMIDAZOLE DERIVATIVES

This invention relates to the use of a particular class of heteroaromatic compounds. More particularly, the invention is concerned with the use of substituted benzimidazole derivatives which are antagonists of dopamine receptor subtypes within the brain and are therefore of benefit in the treatment and/or prevention of psychotic disorders such as schizophrenia.

The "dopamine hypothesis" of schizophrenia predicts an increased activity of dopamine neurotransmission in the disease. The hypothesis is supported by early observations that drugs, such as amphetamine, with dopamine agonist or dopamine-releasing properties are capable of eliciting a psychosis indistinguishable from acute paranoid schizophrenia.

Schizophrenia is a disorder which is conventionally treated with drugs known as neuroleptics. In the majority of cases, the symptoms of schizophrenia can be treated successfully with so-called "classical" neuroleptic agents such as haloperidol. Classical neuroleptics generally are antagonists at dopamine $D_2$ receptors. The fact that classical neuroleptic drugs have an action on dopamine receptors in the brain thus lends credence to the "dopamine hypothesis" of schizophrenia.

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

Notwithstanding their beneficial antipsychotic effects, classical neuroleptic agents such as haloperidol are frequently responsible for eliciting acute extrapyramidal symptoms and neuroendocrine disturbances. These side-effects, which clearly detract from the clinical desirability of classical neuroleptics, are believed to be attributable to $D_2$ receptor blockade in the striatal region of the brain. It is considered (Van Tol et al., supra) that compounds which can interact selectively with the dopamine $D_4$ receptor subtype, whilst having a less-pronounced action at the $D_2$ subtype, might be free from, or at any rate less prone to, the side-effects associated with classical neuroleptics, whilst at the same time maintaining a beneficial level of antipsychotic activity.

The compounds of use in the present invention, being antagonists of dopamine receptor subtypes within the brain, are accordingly of benefit in the treatment and/or prevention of psychotic disorders such as schizophrenia. Moreover, the compounds of use in the invention have a selective affinity for the dopamine $D_4$ receptor subtype over other dopamine receptor subtypes, in particular the $D_2$ subtype, and can therefore be expected to manifest fewer side-effects than those associated with classical neuroleptic drugs.

U.S. Pat. Nos. 3,362,956 and 3,472,854 describe certain 1-[(heterocyclyl)-lower-alkyl]-4-substituted-piperazines, in which the heterocyclyl moiety represents inter alia a benzimidazole group. These compounds are alleged therein to possess a panoply of depressant actions on the autonomic nervous system, the cardiovascular system and the skeletal muscular system (including psychomotor depressant, sedative, adrenolytic, rectal temperature lowering, anticonvulsant, blood pressure lowering and heart force increasing activities), and are consequently alleged to be useful as tranquilizers, sedatives, adrenolytic agents, hypothermic agents, anti-convulsants, hypotensive agents and cardiovascular agents.

In addition, U.S. Pat. No. 3,658,822 describes certain derivatives of [benzimidazolyl-2-methyl]-piperazine, which are stated to exhibit cardiotropic, analgesic, sedative and spasmolytic activities.

Moreover, in Bull. Haffkine Inst., 1978, 6, 62, there is described the preparation, and testing for in vivo anthelmintic activity, of a series of substituted piperazinomethyl benzimidazoles.

There is, however, no suggestion in U.S. Pat. Nos. 3,362,956, 3,472,854 or 3,658,822, nor in Bull. Haffkine Inst., 1978, 6, 62, that the compounds described therein would be of any benefit in the treatment and/or prevention of psychotic disorders such as schizophrenia, still less that in doing so they might be expected to manifest fewer side-effects than those exhibited by classical neuroleptic agents.

The present invention accordingly provides the use of a compound of formula I, or a pharmaceutically acceptable salt thereof or a prodrug thereof:

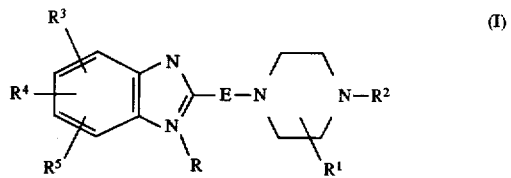

wherein

E represents —$CH_2$— or —$CH_2CH_2$—;

R represents hydrogen or $C_{1-6}$ alkyl;

$R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group; for the manufacture of a medicament for the treatment and/or prevention of psychotic disorders such as schizophrenia.

For use in medicine, the salts of the compounds of formula I will be pharmaceutically acceptable salts. Other salts may, however, be useful in the preparation of the compounds of use in the invention or of their pharmaceutically acceptable salts. Suitable pharmaceutically acceptable salts of the compounds of use in this invention include acid addition salts which may, for example, be formed by mixing a solution of the compound of use in the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of use in the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents R, $R^1$ and $R^2$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$ and $R^2$ include phenyl and naphthyl.

Particular aryl($C_{1-6}$)alkyl groups within the scope of the term "hydrocarbon" and within the definition of the substituents $R^1$ and $R^2$ include benzyl, naphthylmethyl, phenethyl and phenylpropyl.

Suitable heterocycloalkyl groups include azetidinyl, pyrrolidyl, piperidyl, piperazinyl and morpholinyl groups.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl($C_{1-6}$)alkyl groups within the scope of the expression "a heterocyclic group" and within the definition of the substituents $R^1$ and $R^2$ include thienylmethyl, pyridylmethyl, pyrimidinylmethyl and pyrazinylmethyl.

The hydrocarbon and heterocyclic groups, as well as the substituents $R^1$ and $R^2$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, $-NR'R''$, $-NR''COR'''$, $-NR'CO_2R''$, $-NR''SO_2R'''$, $-CH_2NR''SO_2R'''$, $-NHCONR'R''$, $-CONR'R''$, $-SO_2NR'R''$ and $-CH_2SO_2NR'R''$, in which $R'$ and $R''$ independently represent hydrogen, $C_{1-6}$ alkyl, aryl or aryl ($C_{1-6}$) alkyl.

The term "halogen" as used herein includes fluorine, chlorine, bromine and iodine, especially chlorine.

The present invention includes within its scope the use of prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in "Design of Prodrugs", ed. H. Bundgaard, Elsevier, 1985.

Where the compounds of use in the invention have at least one asymmetric centre, they may accordingly exist as enantiomers. Where the compounds of use in the invention possess two or more asymmetric centres, they may additionally exist as diastereoisomers. It is to be understood that the use of all such isomers and mixtures thereof is encompassed within the scope of the present invention.

Suitably, the substituent R represents hydrogen or methyl, especially hydrogen.

Suitably, the substituent $R^1$ represents hydrogen.

Suitable values for the substituent $R^2$ include $C_{1-6}$ alkyl, aryl, aryl($C_{1-6}$)alkyl and heteroaryl, any of which groups may be optionally substituted. Examples of optional substituents on the group $R^2$ include $C_{1-6}$ alkyl, halogen, trifluoromethyl, $C_{1-6}$ alkoxy, nitro, $C_{1-6}$ alkylamino and di($C_{1-6}$)alkylamino.

Particular values of $R^2$ include methyl, ethyl, n-propyl, isopropyl, phenyl, chlorophenyl, ethylphenyl, methoxyphenyl, nitrophenyl, benzyl, chlorobenzyl, phenethyl, phenylpropyl and benzthienyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, ethyl, methoxy and benzyloxy.

A particular sub-class of compounds of use in the invention is represented by the compounds of formula IIA, and pharmaceutically acceptable salts thereof and prodrugs thereof:

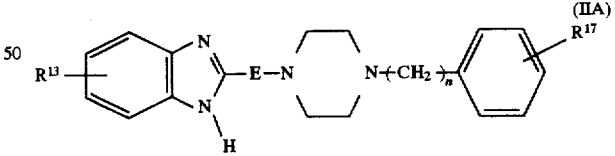

(IIA)

wherein
E is as defined with reference to formula I above;
n is zero, 1, 2 or 3; and
$R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Particular values of $R^{13}$ include hydrogen, fluoro, chloro, methyl, ethyl, methoxy and benzyloxy.

Particular values of $R^{17}$ include hydrogen, chloro, methoxy and nitro.

Another sub-class of compounds of use in the invention is represented by the compounds of formula IIB, and pharmaceutically acceptable salts thereof and prodrugs thereof:

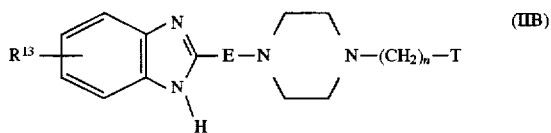

wherein

E is as defined with reference to formula I above;

n and $R^{13}$ are as defined with reference to formula IIA above; and

T represents a group of formula (i), (ii), (iii) or (iv):

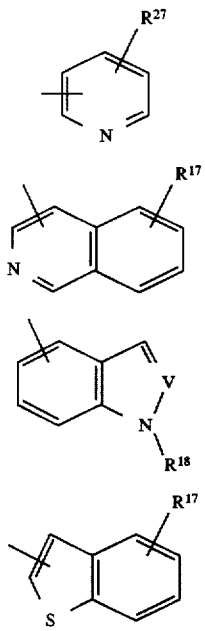

in which

V represents nitrogen or CH;

$R^{17}$ is as defined with reference to formula IIA above;

$R^{18}$ represents hydrogen or methyl; and $R^{27}$ represents $C_{1-6}$ alkyl, halogen, trifluoromethyl, $C_{1-6}$ alkoxy, cyano, nitro, amino, $C_{1-6}$ alkylamino or di($C_{1-6}$) alkylamino.

Suitably, T represents a group of formula (iv).

Suitably, $R^{27}$ is $C_{1-6}$ alkyl or halogen, especially methyl or chloro.

Specific compounds of use in the present invention include:

2-(4-phenylpiperazin-1-ylmethyl)benzimidazole;
2-[4-(4-chlorophenyl)piperazin-1-ylmethyl]benzimidazole;
2-(4-benzylpiperazin-1-ylmethyl)benzimidazole;
2-[2-(4-phenylpiperazin-1-yl)ethyl]benzimidazole;

and pharmaceutically acceptable salts thereof and prodrugs thereof.

Certain compounds falling within the definition of formula I above are novel. A particular sub-class of novel compounds in accordance with the present invention comprises the compounds of formula IIB as defined above, and salts and prodrugs thereof. The present invention further provides a novel compound selected from the following:

2-[4-(4-methoxyphenyl)piperazin-1-ylmethyl] benzimidazole;
2-[4-(2-phenylethyl)piperazin-1-ylmethyl]benzimidazole;
6-chloro-2-(4-phenylpiperazin-1-ylmethyl)benzimidazole;
6-methoxy-2-(4-phenylpiperazin-1-ylmethyl) benzimidazole;
2-[4-(benzothiophen-2-yl)piperazin-1-ylmethyl] benzimidazole;

and salts and prodrugs thereof.

The invention also provides pharmaceutical compositions comprising one or more of the novel compounds according to the invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of schizophrenia, a suitable dosage level is about 0.01 to 250 mg/kg per day, preferably about 0.05 to 1100 mg/kg per day, and especially about 0.05 to 5 mg/kg per day. The compounds may be administered on a regimen of 1 to 4 times per day.

The compounds of formula I above, including the novel compounds according to the present invention, may be prepared by a process which comprises reacting a compound of formula III with a compound of formula IV:

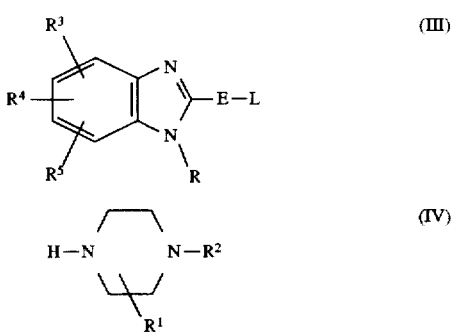

(III)

(IV)

wherein E, R, $R^1$, $R^2$, $R^3$, $R^4$ and $R^5$ are as defined above, and L represents a suitable leaving group.

The leaving group L is suitably a halogen atom, e.g. chlorine.

The reaction is conveniently carried out by stirring the reactants under basic conditions in a suitable solvent, for example potassium carbonate in N,N-dimethylformamide, or triethylamine in tetrahydrofuran or acetonitrile.

In an alternative procedure, the compounds of formula I above, including the novel compounds according to the present invention, may be prepared by a process which comprises reducing a compound of formula V:

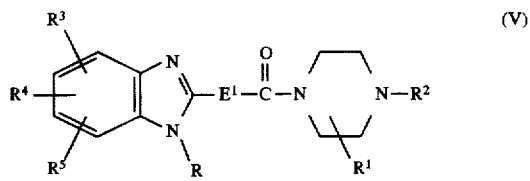

(V)

wherein R, $R^1$, $R^2$, $R^3$, $R^4$ and $R^5$ are as defined above; and $E^1$ represents a bond or a methylene group.

The reaction is conveniently carried out by treating the compound V with a reducing agent such as lithium aluminium hydride in an appropriate solvent, e.g. tetrahydrofuran.

The intermediates of formula V above may suitably be prepared by reacting a compound of formula IV as defined above with a compound of formula VI:

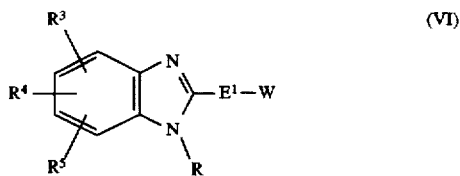

(VI)

wherein R, $R^3$, $R^4$, $R^5$ and $E^1$ are as defined above; and W represents a reactive carboxylate moiety.

Suitable values for the reactive carboxylate moiety W include esters, for example $C_{1-4}$ alkyl esters; acid anhydrides, for example mixed anhydrides with $C_{1-4}$ alkanoic acids; acid halides, for example acid chlorides; and acylimidazoles.

By way of example, the intermediates of formula VI above wherein W is an acid chloride moiety may be prepared by treating the corresponding carboxylic acid derivative with thionyl chloride in toluene. Similarly, the intermediates of formula VI wherein W is an acylimidazole moiety may be prepared by treating the corresponding carboxylic acid derivative with 1,1'-carbonyldiimidazole. Alternatively, the reactive carboxylate moiety W may be obtained by treating the corresponding compound wherein W is carboxy with 1-(3-dimethylaminopropyl)-3-ethylcarbodiimide hydrochloride and 1-hydroxybenzotriazole hydrate, optionally in the presence of triethylamine; the resulting activated carboxylate intermediate may then suitably be reacted in situ with the required compound of formula IV.

Where they are not commercially available, the starting materials of formula III, IV and VI may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 MM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 µM.

EXAMPLE 1

2-[4-(4-Methoxyphenyl)piperazin-1-yl methyl] benzimidazole

Potassium carbonate (2.76 g, 20 mmol) and 2-(chloromethyl)benzimidazole (1.70 g, 10 mmol) were added to a solution of 1-(4-methoxyphenyl)piperazine (1.92 g, 10 mmol) in DMF (20 ml) under a nitrogen atmosphere and the mixture was stirred overnight. The mixture was diluted with water (200 ml) and extracted with ethyl acetate (3×100 ml). The combined organic layers were washed with water (100 ml) and brine (100 ml), dried (MgSO$_4$) and evaporated in vacuo to give a solid which was recrystallised from toluene to give the title compound as a buff solid (731 mg, 23%). mp 214°–216° C.; (Found: C, 70.80; H, 6.82; N, 17.28. C$_{19}$H$_{22}$N$_4$O requires C, 70.78; H, 6.88; N, 17.38%); $\delta_H$ (DMSO-d$_6$) 2.59–2.62 (4H, m, 2×piperazinyl CH$_2$), 3.03–3.05 (4H, m, 2×piperazinyl CH$_2$), 3.67 (3H, s, OCH$_3$), 3.77 (2H, s, CH$_2$N), 6.79–6.82 (2H, m, ArH), 6.85–6.89 (2H, m, ArH), 7.10–7.17 (2H, m, ArH), 7.43 (1H, d, J 6.9 Hz, ArH), 7.55 (1H, d, J 6.9 Hz, ArH), and 12.30 (1H, brs, NH); m/z (CI$^+$, NH$_3$) 323 (M+1)+.

Similarly prepared were:

EXAMPLE 2

2-[4-(4-Chlorophenyl)piperazin-1-yl methyl] benzimidazole

Mp 212°–213° C. (PhMe); (Found: C, 66.19; H, 5.65; N, 17.15. C$_{18}$H$_{19}$ClN$_4$ requires C, 66.15; H, 5.86; N, 17.14%); $\delta_H$ (DMSO-d$_6$) 2.60 (4H, t, J 4.9 Hz, 2×piperazinyl CH$_2$), 3.16 (4H, t, J 4.9 Hz, 2×piperazinyl CH$_2$), 3.77 (2H, s, CH$_2$N), 6.93 (2H, dd, J 7.0 and 2.2 Hz, ArH), 6.99–7.14 (2H, m, ArH), 7.20 (2H, m, ArH), 7.48 (2H, brs, ArH), and 12.31 (1H, brs, NH); m/z (CI+, NH$_3$) 327 (M+1)$^+$.

EXAMPLE 3

2-(4-Phenylpiperazin-1-yl methyl)benzimidazole

Mp>255° C. (dec.) (MeOH); (Found: C, 73.55; H, 6.88; N, 19.11. C$_{18}$H$_{20}$N$_4$ requires C, 73.94; H, 6.90; N, 19.16%); $\delta_H$ (DMSO-d$_6$) 2.62 (4H, t, J 5.0 Hz, 2×piperazinyl CH$_2$), 3.16 (4H, t, J 5.0 Hz, 2×piperazinyl CH$_2$), 3.78 (2H, s, CH$_2$N), 6.77 (1H, t, J 7.0 Hz, 4'-H), 6.92 (2H, d, J 8.0 Hz, 2'-H, 5'-H), 7.16 (4H, m, ArH), 7.44 (1H, d, J 7.0 Hz, ArH), 7.56 (1H, d, J 7.0 Hz, ArH), and 12.33 (1H, brs, NH); m/z (CI$^+$, NH$_3$) 293 (M+1)$^+$.

EXAMPLE 4

2-(4-Benzylpiperazin-1-yl methyl)benzimidazole

Mp 197°–199° C. (PhMe); (Found: C, 73.81; H, 7.21; N, 17.94. C$_{19}$H$_{22}$N$_4$ 0.2H$_2$O requires C, 73.61; H, 7.28; N, 18.07%); $\delta_H$ (DMSO-d$_6$) 2.47–2.51 (8H, m, 4×piperazinyl CH$_2$), 3.46 (2H, s, CH$_2$N), 3.69 (2H, s, CH$_2$N), 7.09–7.16 (2H, m, ArH), 7.21–7.33 (5H, m, ArH), 7.42 (1H, d, J 7.3 Hz, ArH), 7.53 (1H, d, J 7.3 Hz, ArH), and 12.23 (1H, brs, NH); m/z (CI$^+$, NH$_3$) 307 (M+1)$^+$.

EXAMPLE 5

5-Chloro-2-(4-phenylpiperazin-1-yl methyl) benzimidazole

Mp 198°–201° C. (PhMe); (Found: C, 66.15; H, 5.60; N, 16.24%; C$_{18}$H$_{19}$ClN$_4$ requires C, 66.15; H, 5.86; N, 17.14%); $\delta_H$ (CDCl$_3$) 2.78 (4H, t, J 5.0 Hz, 2×piperazinyl CH$_2$), 3.27 (4H, t, J 5.0 Hz, 2 ×piperazinyl CH$_2$), 3.93 (2H, s, NCH$_2$Ar), 6.87–6.94 (3H, m, ArH), 7.18–7.30 (5H, m, ArH), and 7.56 (1H, brs, NH); m/z (CI$^+$, NH$_3$) 327 (M+1)$^+$.

EXAMPLE 6

5-Methoxy-2-(4-phenylpiperazin-1-yl methyl) benzimidazole

Mp 178°–180° C. (PhMe); (Found: C, 71.17; H, 6.69; N, 17.55%; C$_{19}$H$_{22}$N$_4$O requires C, 70.78; H, 6.89; N, 17.38%) $\delta_H$ (CDCl$_3$) 2.76 (4H, t, J 5.0 Hz, 2×piperazinyl CH$_2$), 3.25 (4H, t, J 5.0 Hz, 2×piperazinyl CH$_2$), 3.85 (3H, s, OCH$_3$), 3.89,(2H, s, NCH$_2$Ar), 6.86–6.94 (4H, m, ArH), 7.06 (1H, brs, NH), 7.25–7.29 (3H, m, ArH), and 7.49 (1H, brs, ArH); m/z (CI+, NH.) 323 (M+1)+.

EXAMPLE 7

2-[4-(2-Phenylethyl)piperazin-1-yl methyl] benzimidazole

Mp 150°–152° C. (PhMe); (Found: C, 74.61; H, 7.20; N, 17.33; C$_{20}$H$_{24}$N$_4$ requires C, 74.97; H, 7.55; N, 17.48%); $\delta_H$ (CDCl$_3$) 2.63–2.67 (10H, m, 4×piperazinyl CH$_2$, 1×CH$_2$), 2.82 (2H, t, J 7.0 Hz, CH$_2$), 3.89 (2H, s, NCH$_2$Ar), 7.19–7.31 (9H, m, ArH), and 7.60 (1H, brs, NH); m/z (CI+, NH$_3$) 321 (M+1)+.

EXAMPLE 8

2-[2-(4-Phenylpiperazin-1-yl)ethyl]benzimidazole

Step 1: 2-Benzimidazolylacetic acid

A mixture of 2-benzimidazolylacetonitrile (5.58 g, 35.5 mmol) and 4M sodium hydroxide solution (25 ml) in ethanol (100 ml) was heated at reflux for 8 h. The reaction mixture was concentrated in vacuo, the residue dissolved in water (100 ml), and extracted with ethyl acetate (2×100 ml). The aqueous phase was acidified with dilute hydrochloric acid to pH 4–5, the precipitated solid was filtered, washed with water, and dried to give the title compound (5.97 g, 95%) as a buff solid; $\delta_H$ (DMSO-d$_6$) 2.47 (2H, s, CH$_2$CO$_2$H), 7.09 (2H, m, ArH), 7.39 (1H, brs, ArH), 7.48 (1H, brs, ArH), and 12.13 (1H, brs, NH).

Step 2: 1-(2-Benzimidazol-2-yl)acetyl-4-phenylpiperazine

A mixture of 2-benzimidazolylacetic acid (1.91 g, 10.8 mmol), triethylamine (3.8 ml, 27 mmol), 1-hydroxybenzotriazole (80%; 2.75 g, 16 mmol), 1-phenylpiperazine (2.5 ml, 16 mmol) and 1-(3-dimethylaminopropyl)-3-ethylcarbodiimide hydrochloride (3.11 g, 16.2 mmol) in THF (150 ml) was stirred at room temperature overnight. The reaction mixture was poured into 0.5M citric acid (600 ml) and extracted with ethyl acetate. The citric acid phase was basified to pH5 with 4M sodium hydroxide and the precipitated solid collected. The filtrate was further basified to pH13 and a second crop of solid collected. The precipitated solids were combined, washed with water and dried to give the title compound (1.18 g, 34%) as a beige solid; $\delta_H$ (CDCl$_3$) 3.17 (4H, m, 2×piperazinyl CH$_2$), 3.82 (4H, m, 2×piperazinyl CH$_2$), 4.22 (2H, s, CH$_2$CO), 6.91 (3H, m, ArH), 7.27 (4H, m, ArH), 7.58 (2H, dd, J 6.0, 3.2 Hz, ArH), and 8.95 (1H, brs, NH).

11

Step 3: 2-[2-(4-Phenylpiperazin-1-yl)ethyl]benzimidazole

A solution of lithium aluminium hydride in THF (1.0 M, 2.0 ml, 2.0 mmol) was added to a solution of 1-(2-benzimidazol-2-yl)acetyl- 4-phenylpiperazine (0.56 g, 1.75 mmol) in THF (50 ml) and the mixture stirred at room temperature for 4 h. A second portion of lithium aluminium hydride solution (2.0 ml, 2.0 mmol) was added and the reaction mixture stirred at room temperature for a further 2 h followed by 4 h at reflux. The reaction mixture was allowed to cool and water (0.2 ml), 4M sodium hydroxide (0.2 ml), and water (0.6 ml) added. The solid produced was filtered off, washing through with dichloromethane. The filtrate was concentrated in vacuo and the residue purified by flash chromatography eluting with 10% methanol, 30% dichloromethane in ethyl acetate to afford the title compound (0.24 g, 45%). This material was recrystallised from ethyl acetate to give a crystalline solid, mp 201°–203° C.; (Found: C, 73.99; H, 7.32; N, 18.05. $C_{19}H_{22}N_4$ $0.1H_2O$ requires C, 74.04; H, 7.26; N, 18.18%); $\delta_H$ (DMSO-$d_6$) 2.60 (4H, m, 2×piperazinyl $CH_2$), 2.83 (2H, t, J 7.5 Hz, $ArCH_2CH_2N$), 3.02 (2H, t, J 7.5 Hz, $ArCH_2CH_2N$), 3.13 (4H, m, 2×piperazinyl $CH_2$), 6.76 (1H, t, J 7.2 Hz, ArH), 6.92 (2H, m, ArH), 7.11 (2H, m, ArH), 7.20 (2H, dd, J 8.7, 7.2 Hz, ArH), 7.42 (1H, m, ArH), 7.50 (1H, m, ArH), and 12.15 (1H, brs, NH); m/z (CI+, $NH_3$) 307 $(M+H)^+$.

EXAMPLE 9

2-[4-(Benzothiophen-2-yl)piperazin-1-yl]methylbenzimidazole

Step 1: 1-Benzyl-4-(benzothiophen-2-yl)piperazine

To a solution of 2-mercaptobenzothiophene (1.8 g, 10.8 mmol) in toluene under nitrogen was added N-benzylpiperazine (1.88 ml, 10.8 mmol) and the mixture heated at reflux for 1.5 h. Left to cool, concentrated in vacuo and product recrystallised from diethyl ether-hexane to yield the title compound (1.55 g), m.p. 160°–161° C.

Step 2: 1-(Benzothiophen-2-yl)piperazine hydrochloride

To a solution of 1-benzyl-4-(benzothiophen-2-yl)piperazine (1.5 g, 4.9 mmol) in anhydrous dichloromethane (20 ml) at 0° C. under nitrogen was added 1-chloroethylchloroformate (0.68 ml, 6.37 mmol). The mixture was allowed to warm to room temperature, stirred for 1 h and concentrated in vacuo. The crude residue was dissolved in methanol (10 ml) and heated to reflux for 30 minutes, left to cool and the title compound collected by filtration (0.6 g), m.p. 240° C. (dec.).

Step 3: 2-[4-(Benzothiophen-2-yl)piperazin-1-yl]methylbenzimidazole

The title compound was prepared in an analogous manner to Example 1. Using 2-chloromethylbenzimidazole (0.36 g, 2.1 mmol) and 2-(benzothiophen-2-yl)piperazine hydrochloride (0.5 g, 1.9 mmol) gave the title compound (265 mg, 40%), m.p. 242° C. (dec.); (Found: C, 69.04; H, 5.78; N, 15.83. $C_{20}H_{20}N_4S$ requires C, 68.94; H, 5.79; N, 16.08%); δH (DMSO-$d_6$) 2.65 (4H, t, J 5 Hz, 2×piperazinyl $CH_2$), 3.26 (4H, t, J 5 Hz, 2×piperazinyl $CH_2$), 3.80 (2H, s, $ArCH_2N$), 6.30 (1H, s, benzothiophene 3-H), 7.02–7.23 (4H, m, ArH), 7.45 (2H, d, J 8 Hz, ArH), 7.57 (1H, d, J 8 Hz, ArH), 7.66 (1H, d, J 8 Hz, ArH), and 12.30 (1H, br s, NH); m/Z (CI+, $NH_3$) 349 $(M+1)^+$.

We claim:

1. A method for the treatment and/or prevention of psychotic disorders comprising the step of administering to a patient in need thereof a compound of formula I, or a pharmaceutically acceptable salt thereof:

12

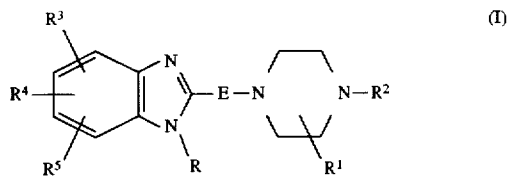

(I)

wherein

E represents $-CH_2-$ or $-CH_2CH_2-$;

R represents hydrogen or $C_{1-6}$ alkyl;

$R^1$ represents hydrogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$; and $R^a$ and $R^b$ independently represent hydrogen, hydrocarbon or a heterocyclic group.

2. The use as claimed in claim 1 of a compound represented by formula IIA, and pharmaceutically acceptable salts thereof:

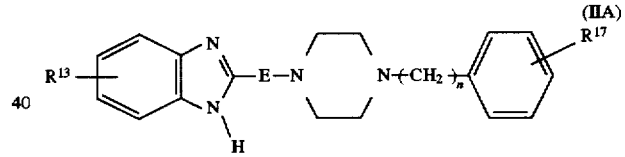

(IIA)

wherein

E is as defined in claim 1;

n is zero, 1, 2 or 3; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl.

3. The method as claimed in claim 1 wherein the compound is selected from:

2-(4-phenylpiperazin-1-ylmethyl)benzimidazole;

2-[4-(4-chlorophenyl)piperazin-1-ylmethyl]benzimidazole;

2-(4-benzylpiperazin-1-ylmethyl)benzimidazole;

2-(4-phenylpiperazin-1-yl)ethyl]benzimidazole;

2-[4-(4-methoxyphenyl)piperazin-1-ylmethyl]benzimidazole;

2[4-(2-phenylethyl)piperazin-7-ylmethyl]benzimidazole;

6-chloro-2-(4-phenylpiperazin-1-ylmethyl)benzimidazole;

6-methoxy-2-(4-phenylpiperazin-1-ylmethyl)benzimidazole;

and phamaceutically acceptable salts thereof.

4. A compound of formula IIB, or a salt thereof:

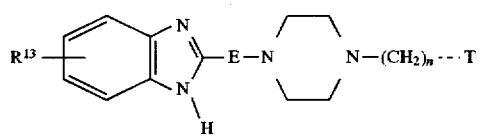

wherein

E represents —CH$_2$— or —CH$_2$CH$_2$—;

n is zero, 1, 2 or 3 and R$^{13}$ represents hydrogen, halogen, cyano, nitro, trifluoromethyl, amino, C$_{1-6}$ alkylamino, di(C$_{1-6}$)alkylamino, C$_{1-6}$ alkyl, C$_{1-6}$ alkoxy, aryl(C$_{1-6}$) alkoxy or C$_{2-6}$ alkylcarbonyl; and T represents a group of formula (i), (ii), (iii) or (iv):

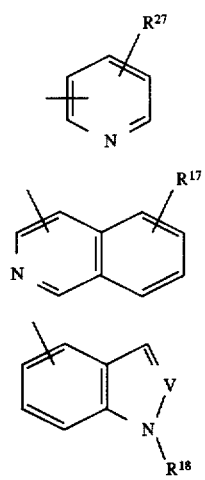

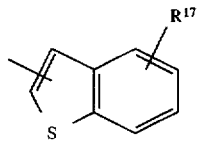

in which

V represents nitrogen or CH;

R$^{17}$ represents hydrogen, halogen, cyano, nitro, trifluoromethyl, amino, C$_{1-6}$ alkylamino, di(C$_{1-6}$) alkylamino, C$_{1-6}$ alkyl, C$_{1-6}$ alkoxy, aryl(C$_{1-6}$)alkoxy or C$_{2-6}$ alkylcarbonyl;

R$^{18}$ represents hydrogen or methyl; and

R$^{27}$ represents C$_{1-6}$ alkyl, halogen, trifluoromethyl, C$_{1-6}$ alkoxy, cyano, nitro, amino, C$_{1-6}$ alkylamino or di(C$_{1-6}$)alkylamino.

5. A pharmaceutical composition comprising a compound as claimed in claim 4 in association with a pharmaceutically acceptable carrier.

6. A method for the treatment and/or prevention of psychotic disorders, which comprises administering to a patient in need of such treatment an effective amount of a compound as claimed in claim 4.

7. The compound of claim 4 being:

2-[4-(benzothiophen-2-yl)piperazin-1-ylmethlyl]-benzimidazole.

8. A pharmaceutical composition comprising a compound as claimed in claim 7 in association with a pharmaceutically acceptable carrier.

9. A method for the treatment of psychotic disorders, which comprises administering to a patient in need of such treatment, al effective amount of a compound as claimed in claim 7.

* * * * *